United States Patent [19]

Pappano

[11] Patent Number: 4,574,634
[45] Date of Patent: Mar. 11, 1986

[54] AUTOMATIC PAPER TESTING APPARATUS

[75] Inventor: Dominic A. Pappano, Cambridge, Mass.

[73] Assignee: Westvaco Corporation, New York, N.Y.

[21] Appl. No.: 639,085

[22] Filed: Aug. 9, 1984

[51] Int. Cl.$^4$ ............................................. G01N 29/00
[52] U.S. Cl. ........................................ 73/597; 73/159
[58] Field of Search ................. 73/597, 159, 641, 634, 73/618

[56] References Cited

U.S. PATENT DOCUMENTS

| | | | |
|---|---|---|---|
| 3,910,104 | 10/1975 | Davies | 73/641 |
| 4,106,327 | 8/1978 | Adler et al. | 73/597 |
| 4,291,577 | 9/1982 | Baum et al. | 73/597 |
| 4,455,872 | 6/1984 | Kossuff et al. | 73/618 |

OTHER PUBLICATIONS

J. K. Carver & D. L. Taylor, "Nondestructive Sonic Measurement of Paper Elasticity," *Tappi*, vol. 48, No. 3, Mar. 1965, p. 142.
E. P. Papadakis, "Ultrasonic Methods for Modulus Measurement in Paper," *Tappi*, vol. 56, No. 2, Feb. 1973, p. 74.
G. A. Baum & L. R. Bornhoeft, "Estimating Poisson Ratios in Paper Using Ultrasonic Techniques," *Tappi*, vol. 62, No. 5, May 1979, p. 87.
R. W. Mann, G. A. Baum, and C. C. Habeger, "Elastic Wave Propagation in Paper," *Tappi*, vol. 62, No. 8, Aug. 1979, p. 115.
R. W. Mann, G. A. Baum, and C. C. Habeger, "Determination of All Nine Orthotropic Elastic Constants for Machine-Made Paper," *Tappi*, vol. 63, No. 2, Feb. 1980, p. 163.
G. A. Baum and C. C. Habeger, "On-Line Measurement of Paper Mechanical Properties," *Tappi*, vol. 63, No. 7, Jul. 1980, p. 63.
G. A. Baum, D. C. Brennan, and C. C. Habeger, "Orthotropic Elastic Constants of Paper," *Tappi*, vol. 64, No. 8, Aug. 1981, p. 97.
G. A. Baum, "Procedures for Measuring the In-Plane Orthotropic Elastic Constants of Paper Using Ultrasonic Techniques," The Institute of Paper Chemistry, Appleton, WI, IPC Technical Paper Series, No. 119, Dec. 1981.

*Primary Examiner*—Anthony V. Ciarlante
*Attorney, Agent, or Firm*—W. A. Marcontell; R. L. Schmalz

[57] ABSTRACT

A fully automatic test system is provided to nondestructively determine the elastic constant information of paper samples. Two ultrasonic wave sensors are mounted in alignment with the instrument frame at respective distances from an ultrasonic generator. A motor driven turntable beneath the sensors and generator supports a paper test specimen for automatic progression of the specimen fiber orientation relative to the sonic wave propogational direction. Electronic data processing equipment resolve ultrasonic emission and reception signals for quantitative determination of the sonic velocity through four directional transmission modes of a specimen. Such sonic velocity data enables determination of four in-plane elastic parameters.

5 Claims, 11 Drawing Figures

AUTOMATIC PAPER TESTING APPARATUS

BACKGROUND OF THE INVENTION

1. Field of the Invention

The present invention relates to nondestructive testing of paper for mechanical properties. More particularly, the present invention relates an apparatus for testing paper ultrasonically.

2. Prior Art

Paper and paperboard strength properties are important to most converting and end-use applications. Mechanical parameters such as ultimate tensile strength, burst, and bending stiffness are the strength indicia of greatest concern to the papermaker.

Tests to ascertain these mechanical characteristics of a given paper web have, traditionally, been destructive of the test sample or specimen. Loss of the sample is of no consequence but the quantity of specialized test equipment, skills and time required to perform the full battery of such tests is enormous when it is considered that a reliable test average requires a large number of test samples.

Over the past decade, nondestructive ultrasonic methods have been developed to measure many of the mechanical properties previously measured by destructive tests. By these methods, an ultrasonic wave train is transmitted through a sample sheet and the resultant wave velocity is measured. Four independent velocity measurements are taken relative to the test sample fiber orientation and used to calculate the in-plane elastic parameters of the sheet.

Development of this ultrasonic test method has followed two basic avenues. First, "breadboard" type of instrumentation has been assembled for accumulating proof of concept data. Second, instruments are being developed to exploit the concept for continuous data acquisition on a production papermachine.

Apparently overlooked in the ultrasonic test method development are instruments that are specially suited to the needs of a quasi production laboratory where numerous test samples are required to analyze pulp refining or chemical treatment changes. Such test samples are obtained from small, laboratory scale papermachines or as hand sheets formed manually, although rapidly, from an experimental pulp. Continuous production instruments are irrelevant as there is no continuous source of the test subject.

Although a "breadboard" instrument is capable of more data per unit of time than destructive testing, approximately one hour per sample remains as a considerable time investment for the 100 to 200 samples required of a raw stock experiment.

It is therefore, an object of the present invention to provide an automated ultrasonic paper testing machine capable of determining the four in-plane elastic constants of a given sample with a total sample process time of less than fifteen minutes.

SUMMARY

These and other objects of the invention are accomplished by the present invention which includes an ultrasonic transmitter flanked by two receivers at respective distances from the transmitter mounted over a turntable platform. Such mounting is in a diametric line across the turntable rotational center and includes mechanism for simultaneously lifting the three transducer styli off the surface of a turntable mounted sample. The transducer lifting mechanism will also rotate the orientation direction of the transducers by 90°.

Working in coordination with the transducer mechanism is the turntable rotational drive which automatically indexes the sample sheet orientation relative to the transducer mounting line sequentially from an origin position, to a 45° position, to a 90° position and back to the origin position.

At each of four data-taking condition positions, in-plane sonic wave velocity data is automatically calculated and stored. Upon completion of the four position cycle, all stored data is automatically processed to numerically issue the five in-plane elastic constants respective to the tested sample.

BRIEF DESCRIPTION OF THE DRAWINGS

Relative to the drawings wherein like reference characters designate like or similar elements throughout the several figures of the drawings.

DESCRIPTION OF THE PREFERRED EMBODIMENT

Figure 1:
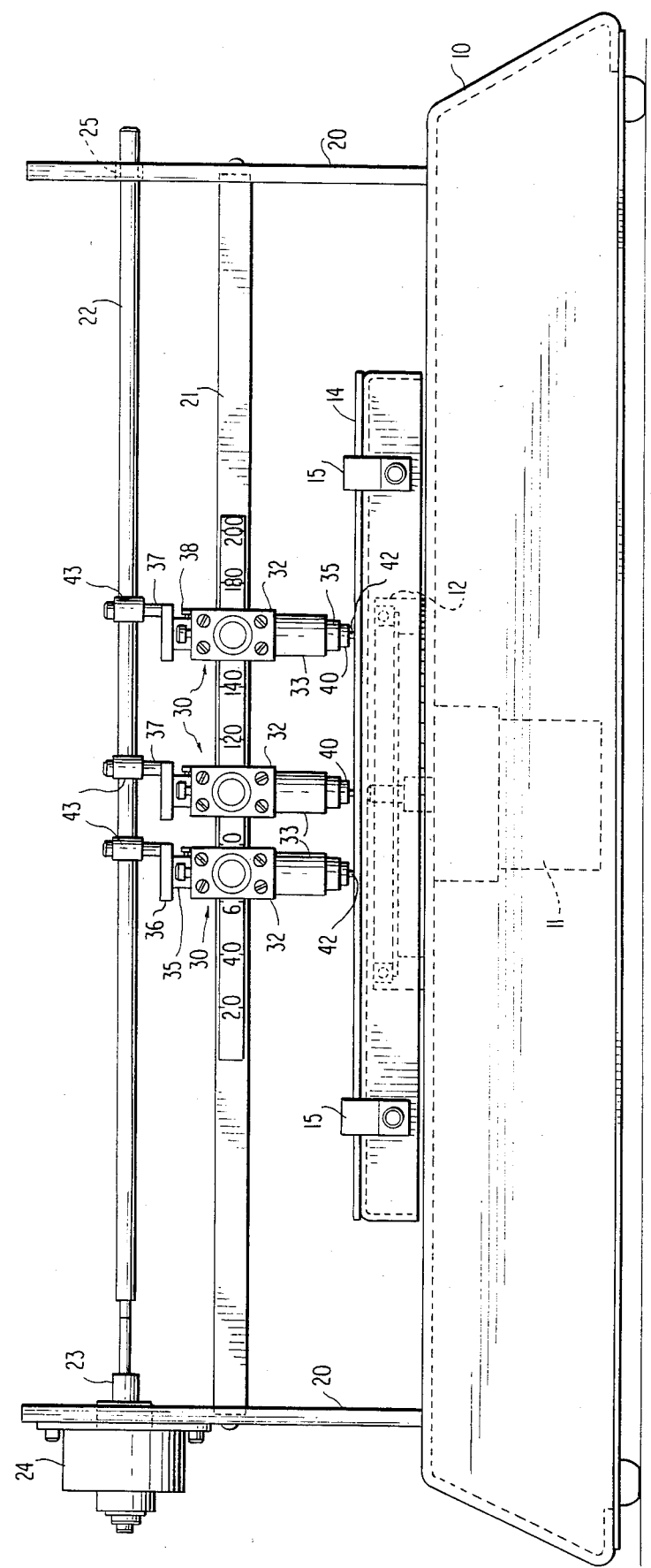
FIG. 1 is a front elevational view of the present invention.
Figure 2:
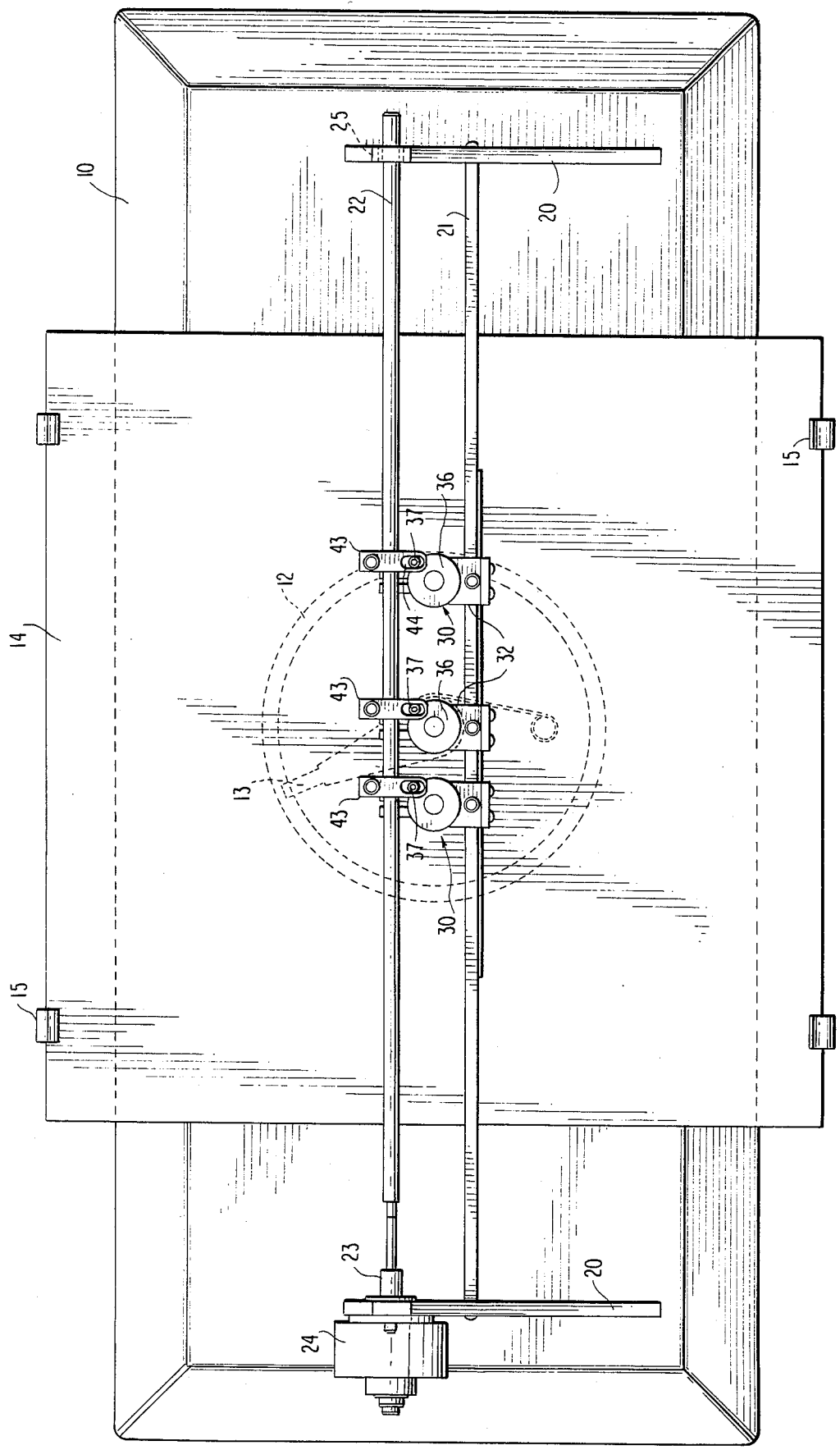
FIG. 2 is a plan view of the present invention.

FIGS. 1 and 2 of the drawings illustrate the base 10 of the present invention as a housing which encloses a turntable drive stepping motor 11. A drive ring 12 and radius arm 13 connect the turntable 14 to a stepping motor 11.

The turntable 14 is dimensioned to receive the desired size of paper sample which is normally 12×12 inches. Spring clips 15 secure the sample to the turntable during a test sequence.

In operation, the turntable 14 will rotate sequentially from a starting position, to a 45° rotation position, to a 90° rotation position and back to the starting position. A stepping motor, which gives a precise increment of angular rotation for each square wave actuating pulse of electrical energy, is ideally suited to the task which requires such accuracy, repetitively.

Brackets 20 secured to the top face of the base 10 support a calibrated slide beam 21 and a linear actuating rod 22. One end of the actuating rod 22 is socketed into a hub cam 23 driven by a stepping motor 24. The frame of motor 24 is rigidly secured to the bracket 20.

The objective served by the hub cam 23 is to axially reciprocate the actuating rod 22 over a fixed stroke length as the stepping motor 24 rotates. Consistent with this action, the rod journal 25 which supports the rod 22 at the opposite bracket 20 is merely a cylindrical sleeve.

Figure 5:
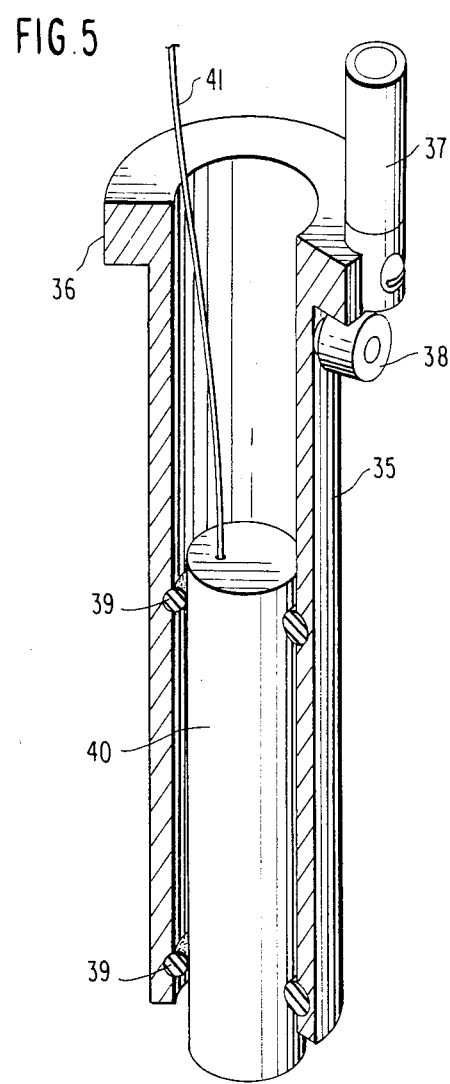
FIG. 5 is a partially sectioned view of the transducer assembly.

Secured to slide beam 21 by slide clamps 32 are three ultrasonic transducer units 30. These are illustrated in detail by FIGS. 3-5.

Each transducer unit 30 comprises an outer sleeve 33 to which the slide clamp 32 is secured. The upper end of the outer sleeve 33 is profiled to include a cam lobe 34.

Coaxially slidable and rotatable within the bore of outer sleeve 33 is disposed an inner sleeve 35. At the upper end of inner sleeve 35 is an external shoulder ring 36 having an upstanding yoke pin 37. Below the shoulder ring 36, a roller follower 38 is secured to the side of the inner sleeve 35 barrel. This roller follower 38 positions the inner sleeve 35 axially within the outer sleeve 33 by riding on the upper profiled edge of the outer sleeve.

Figure 3:
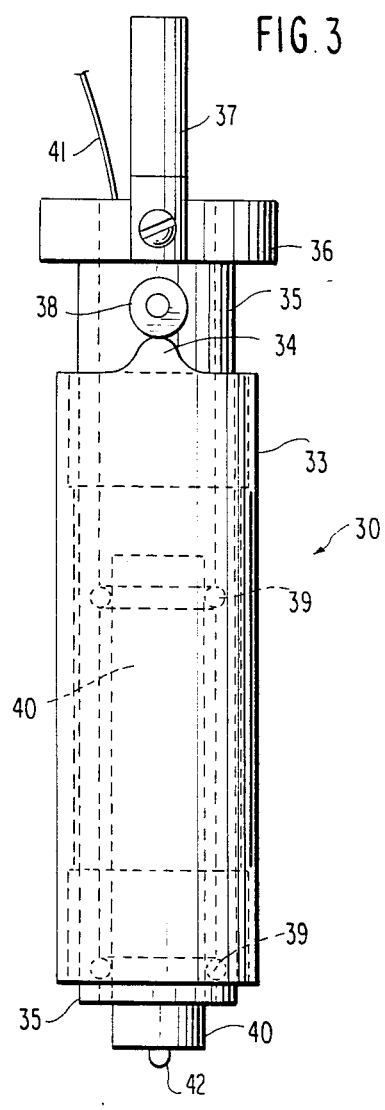
FIG. 3 is an assembly detail of a transducer unit.
Figure 4:
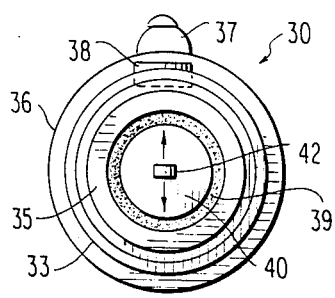
FIG. 4 is a bottom end view of the transducer assembly.

Within the inside bore of the inner sleeve 35 are provided a pair of axially spaced O-rings 39 which serve as resilient, frictional sockets for the ultrasonic transducer head 40 which, representatively, may be an H. M. Morgan Co. model WGRT-5FM. The transducer 40 is serviced by an electrical power lead 41. FIGS. 3 and 4 illustrate the transmission stylus 42 of the transducer 40 which ocillates in the single plane shown by the directional arrows of FIG. 4.

Figure 6:
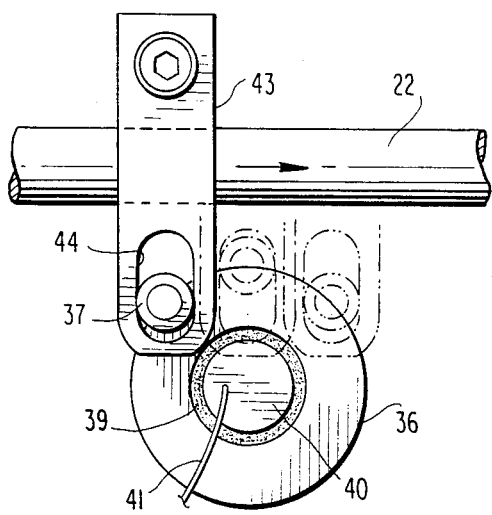
FIG. 6 is a top end view of the transducer assembly.

To the linear actuating rod are clamped respective yokes 43 having pin slots 44 elongated in the direction perpendicular to the actuating rod axis as shown by FIG. 6. These yokes 43 are positioned along the length of rod 22 to receive respective transducer rotating pins 37 within the pin slots 44 of yokes 43.

Operatively, the stroke displacement of rod 22 provided by rotation of the hub cam 23 is sufficient to rotate the inner sleeve transducer unit over an arc of 90° by means of the interconnecting yoke 43 and pin 37. See FIG. 6. One objective served by such 90° rotation is to reorient the oscillation plane of the transducer stylus 42. Another objective served by rotating the transducer unit is the sleeve lifting result of riding over the cam lobe 34.

Figure 11:
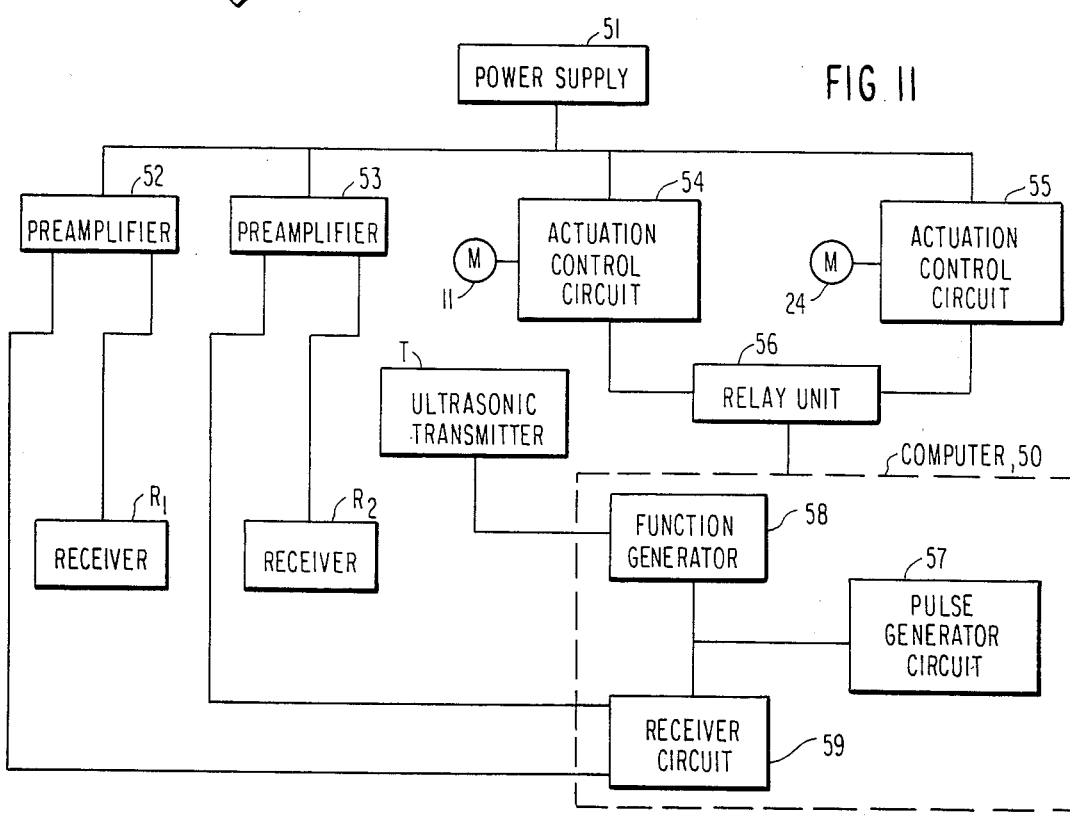

FIG. 11 schematically illustrates the associated electronic equipment necessary to interface the invention power equipment with a computer 50. Broadly described, such equipment includes a power supply 51 and preamplifiers 52 and 53 for the signal outputs respective to receive transducers $R_1$ and $R_2$. The stepping motors 11 and 24 each require actuation control circuits 54 and 55, respectively. A relay unit 56 responds to the appropriate computer signal to initiate the respective motor actuating control circuits. A pulse generator circuit 57 powered by the computer power source emits a square wave "trigger" signal for the transducer emitting and receiving signal functions. Upon receiving the "trigger" signal, the function generator 58 emits the appropriate excitation signal to the ultrasonic transmitter T. Simultaneously, the "trigger" signal emergizes the receiver circuit 59 which is a dedicated digital memory oscilloscope circuit having the capacity to measure the signal receipt time delay respective to the receivers $R_1$ and $R_2$. This time delay between the two receiver transducers $R_1$ and $R_2$ is used to mutually cancel system induced error. The absolute instant of sonic wave emission is irrelevant to the measured time differential between wave reception instants respective to the two receivers.

When programmed with the sonic frequency of signal emission and the differential distance of the two receiving transducers 40 from the transmitter, the sonic wave velocity through the respective sample may be calculated.

To determine all four of the in-plane elastic properties, it is necessary to find the sonic wave transmission velocity in the sample machine direction and cross-machine direction of fiber orientation relative to the direction of sonic wave propogation. Four physical condition sets are required. These four sets are shown by FIGS. 7 through 10.

Figure 7:
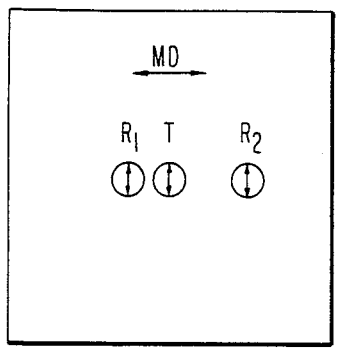
FIGS. 7 through 10 show the relative orientation of a sample sheet to the transducer units in a progressive test sequence; and, FIG. 11 is an electrical schematic of the invention drive components with a computer control unit.

In FIG. 7, the sample square is oriented relative to the ultrasonic transducers so that the direction of transducer stylus 42 displacement is transverse to the fiber machine direction. However, the three transducers are aligned relative to each other parallel with the fiber machine direction. This is the shear configuration of wave propogation and the wave velocity obtained therefrom is designated $C_s$.

Figure 8:
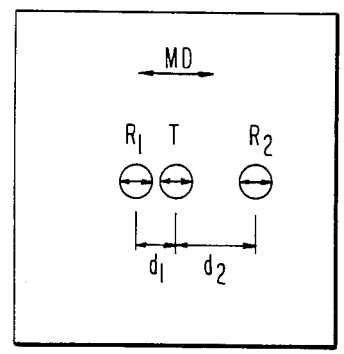

In FIG. 8, the direction of stylus 42 displacement is rotated 90° to parallel alignment with the fiber machine direction and parallel with the transducer alignment. The wave velocity obtained from this configuration is the longitudinal machine direction velocity $C_x$.

Figure 9:
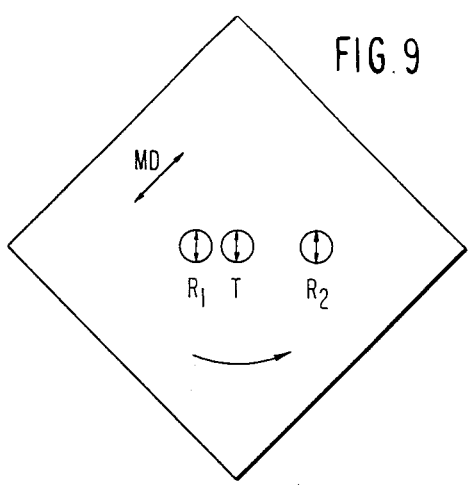

FIG. 9 shows the transducer stylus 42 displacement returned to a perpendicular orientation relative to the three transducer alignment but the turntable 14 is rotated 45° to align the sample fiber machine direction at that angle relative to the wave propogation direction. In this configuration, the 45° shear velocity, $C_{45}$, is obtained.

Figure 10:
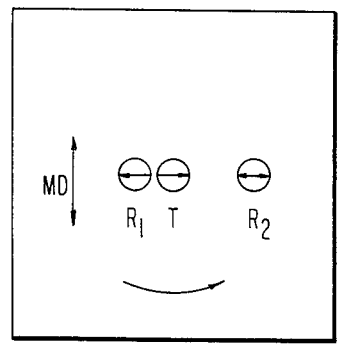

The fourth measuring configuration of the invention is shown by FIG. 10 which has the stylus displacement direction aligned parallel with the transducer alignment but perpendicular to the sample fiber machine direction. This configuration provides the longitudinal cross-machine direction velocity $C_y$, of the wave.

In each of the foregoing measurements the wave velocity, C, is obtained as the quotient of the linear distance difference of the receiver transduces $R_1$ and $R_2$ from the wave emissive transducer T divided by the elapsed time difference of signal receipt by the receivers $R_1$ and $R_2$.

$$C = \frac{d_2 - d_1}{t_2 - t_1}$$

From these four velocity measurements, it is possible to obtain the following web strength properties from these relationships:

1. Young's Modulus, machine direction, $E_x$ $$E_x = \rho C_x^2 (1 - \nu_{xy}\nu_{yx})$$

2. Young's Modulus, cross-machine direction, $E_y$ $$E_y = \rho C_y^2 (1 - \nu_{xy}\nu_{yx})$$

3. Shear Modulus, $G_{xy}$ $$G_{xy} = \rho C_s^2$$

4. Poisson Ratio, xy $$\nu_{xy} = \nu_{yx}\left(\frac{E_y}{E_x}\right)$$

$$\nu_{xy} = \frac{1}{B}\left(1 + \frac{4B^2}{A^2} - \frac{2B^2}{A} - \frac{2B^2}{AR} - \frac{4B}{A} + \frac{B^2}{R} + \frac{B}{R} + B\right)^{\frac{1}{2}} - \frac{1}{B}$$

where:

$$B = \left(\frac{C_x}{C_s}\right)^2$$

$$A = \left(\frac{C_x}{C_{45}}\right)^2$$

$$R = \left(\frac{C_x}{C_y}\right)^2$$

$$v_{xy} = \frac{v_{yx}}{R}$$

$\rho$ = apparent density

In full cycle sequence, a sample sheet is placed on the turntable in the orientation shown by FIG. 7. The actuating rod will have the transducer heads 40 turned to the intermediate position relative to FIG. 6 which positions the roller follower 38 on the cam lobe 34 thereby lifting the transducer stylus 42 off the sample surface.

Upon starting the sequence, stepping motor 24 will stroke the actuating rod 22 to the stylus orientation position of FIG. 7 and into physical contact with the sample surface. When set, the transmitting transducer T is momentarily energized and the receiver responses processed for wave velocity $C_s$ determination. The result is stored in the computer memory for future use.

Upon completion of the $C_s$ subcycle, stepping motor 24 is actuated to stroke rod 22 and rotate the transducers 40 to the FIG. 8 orientation position. When positioned the transducer energizing circuits are initiated and the $C_x$ velocity determined. The result is memory stored.

For the next subcycle, the stepping motor 24 is actuated to set the transducers 40 at the intermediate, raised position. Turntable stepping motor 11 is then actuated to rotate the turntable 14 at the 45° angle position shown by FIG. 9. With the turntable position change complete, stepping motor 24 is again actuated to set the transducer styli down onto the sample surface in the orientation of FIG. 9. So positioned, the transducers are energized and the $C_{45}$ wave velocity determined and stored.

For the next subcycle, the transducers 40 are lifted from the sample surface again and the sample table rotated to complete a 90° displacement from the angle of origin as shown by FIG. 10. When the transducer styli are returned to contact with the sample it is in the orientation of FIG. 10 which is relative parallelism and perpendicular to the sample fiber machine direction. In this configuration, the longitudinal velocity parameter $C_y$ is determined and memory stored.

All four wave velocity values having been determined, the turntable 14 is returned to the starting position of FIG. 7 and the transducers rotated to the raised or sample disengagement position.

At this point in the cycle, the computer begins a programmed calculation sequence using the stored wave velocity data to determine the A, B and R factors in the Poisson's Ratio relationship of $v_{xy}$. From this conclusion, all other moduli may be determined for electronic display or paper printout.

Having fully described my invention,

I claim:

1. An apparatus for sonically determining the strength moduli of a sheet of paper comprising:
   (a) a planar surface turntable for mounting a subject paper sample thereon, said turntable being rotatable about a central axis perpendicular to said planar surface and having rotational stop positions at a point of angular origin, a point of rotation 45° away from said origin position and a rotational point 90° away from said origin position;
   (b) a supporting base for said turntable;
   (c) a pair of bracket arms projecting from said base on substantially opposite sides of said turntable;
   (d) a slide beam secured between the distal ends of said brackets above said turntable;
   (e) at least three sonic transducer units secured to said slide beam in parallel alignment therewith by suspension means, each of said transducer units having a directionally oriented sonic wave simulation stylus disposed thereon for selective engagement with the surface of a paper sample on said turntable, said suspension means comprising means to simultaneously disengage the styli of said transducers from said paper sample surface and to rotate said styli for angular displacement of said orientation direction.

2. An apparatus as described by claim 1 wherein said suspension means comprises linear stroking means for engaging said styli with said paper sample in a first directional orientation alignment at one end of a stroke length, for engaging said styli with said paper sample in a second directional orientation alignment 90° rotated from said first at the other end of said stroke length and for withdrawing said styli from engagement with said paper sample at an intermediate position between said ends.

3. An apparatus as described by claim 1 comprising data processing means and drive means respective to said turntable rotation and said stroking means, said data processing means being connected with said drive means to control the orientation of said styli relative to the orientation of said paper sample.

4. An apparatus as described by claim 3 wherein said data processing means is connected with said transducer units to control the excitation on one sonic transducer unit and receive signals from the other transducer units.

5. An apparatus as described by claim 4 wherein said data processing means is programmed to coordinate said transducer unit excitation and reception with the orientation of said paper sample and said styli.

* * * * *